United States Patent
Choi et al.

(10) Patent No.: US 8,174,695 B2
(45) Date of Patent: May 8, 2012

(54) ARRAYED MICRO-RING SPECTROMETER SYSTEM AND METHOD OF USE

(75) Inventors: Sang H. Choi, Poquoson, VA (US);
Yeonjoon Park, Yorktown, VA (US);
Glen C. King, Williamsburg, VA (US);
James R. Elliott, Vesuvius, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 407 days.

(21) Appl. No.: 12/508,018

(22) Filed: Jul. 23, 2009

(65) Prior Publication Data
US 2010/0039644 A1      Feb. 18, 2010

Related U.S. Application Data

(60) Provisional application No. 61/089,226, filed on Aug. 15, 2008.

(51) Int. Cl.
*G01J 3/28*      (2006.01)
(52) U.S. Cl. ........................................... 356/328
(58) Field of Classification Search .................. 356/326, 356/328; 359/565
See application file for complete search history.

(56) References Cited

U.S. PATENT DOCUMENTS

| | | |
|---|---|---|
| 3,107,270 A | 10/1963 | Hildebrand |
| 3,454,338 A | 7/1969 | Girard et al. |
| 3,603,685 A | 9/1971 | Heflinger et al. |
| 3,649,837 A | 3/1972 | Lehovec |
| 4,429,411 A | 1/1984 | Smither |
| 4,572,616 A | 2/1986 | Kowel et al. |
| 4,743,083 A | 5/1988 | Schimpe |
| 4,752,130 A | 6/1988 | George et al. |
| 4,775,967 A | 10/1988 | Shimada et al. |
| 4,822,148 A | 4/1989 | Agostinelli et al. |
| 4,909,626 A | 3/1990 | Purvis et al. |
| 4,995,714 A | 2/1991 | Cohen |
| 5,011,284 A | 4/1991 | Tedesco et al. |
| 5,071,253 A | 12/1991 | Chase |
| 5,121,378 A | 6/1992 | Hirose et al. |

(Continued)

OTHER PUBLICATIONS

Yeonjoon Park, et al., "Miniaturization of Fresnel spectrometer", Journal of Opt. A: Pure Appl. Opt. 10, Aug. 27, 2008, pp. 1-8.

(Continued)

*Primary Examiner* — Kara E Geisel
(74) *Attorney, Agent, or Firm* — Thomas K. McBride, Jr.; Linda B. Blackburn

(57) ABSTRACT

A spectrometer system includes an array of micro-zone plates (MZP) each having coaxially-aligned ring gratings, a sample plate for supporting and illuminating a sample, and an array of photon detectors for measuring a spectral characteristic of the predetermined wavelength. The sample plate emits an evanescent wave in response to incident light, which excites molecules of the sample to thereby cause an emission of secondary photons. A method of detecting the intensity of a selected wavelength of incident light includes directing the incident light onto an array of MZP, diffracting a selected wavelength of the incident light onto a target focal point using the array of MZP, and detecting the intensity of the selected portion using an array of photon detectors. An electro-optic layer positioned adjacent to the array of MZP may be excited via an applied voltage to select the wavelength of the incident light.

14 Claims, 4 Drawing Sheets

U.S. PATENT DOCUMENTS

| | | |
|---|---|---|
| 5,204,516 A | 4/1993 | Opheij |
| 5,268,973 A | 12/1993 | Jenevein |
| 5,357,591 A | 10/1994 | Jiang et al. |
| 5,360,973 A | 11/1994 | Webb |
| 5,731,874 A | 3/1998 | Maluf |
| 5,793,488 A | 8/1998 | Kulawiec et al. |
| 5,986,758 A | 11/1999 | Lyons et al. |
| 5,995,221 A | 11/1999 | Slutter et al. |
| 6,167,016 A | 12/2000 | Block et al. |
| 6,226,083 B1 | 5/2001 | Schwerzel et al. |
| 6,269,066 B1 | 7/2001 | Chase |
| 6,335,625 B1 | 1/2002 | Bryant et al. |
| 6,366,547 B1 | 4/2002 | Chase |
| 6,452,675 B1 | 9/2002 | Muller et al. |
| 6,509,559 B1 | 1/2003 | Ulrich et al. |
| 6,518,555 B1 | 2/2003 | Kikuchi et al. |
| 6,583,873 B1 | 6/2003 | Goncharov et al. |
| 6,597,452 B1 | 7/2003 | Jiang et al. |
| 6,643,065 B1 | 11/2003 | Silberman |
| 6,762,839 B2 | 7/2004 | Zeylikovich et al. |
| 6,777,656 B2 | 8/2004 | Narita et al. |
| 6,785,201 B2 | 8/2004 | Shinohara et al. |
| 6,847,447 B2 | 1/2005 | Ozanich |
| 6,856,406 B2 | 2/2005 | Chase |
| 6,947,453 B2 | 9/2005 | Sidorin |
| 6,995,840 B2 | 2/2006 | Hagler |
| 6,999,165 B2 | 2/2006 | Hagler |
| 7,072,442 B1 | 7/2006 | Janik |
| 7,084,972 B2 | 8/2006 | Treado |
| 7,106,664 B2 | 9/2006 | Hasegawa et al. |
| 7,158,228 B2 | 1/2007 | Psaltis et al. |
| 7,161,673 B2 | 1/2007 | Da Silva |
| 7,196,791 B2 | 3/2007 | Johansen et al. |
| 7,253,958 B2 | 8/2007 | Aizenberg et al. |
| 7,262,917 B2 | 8/2007 | Yang et al. |
| 7,576,855 B2 * | 8/2009 | Tsukuda .................. 356/326 |
| 7,630,287 B2 | 12/2009 | Oumi et al. |
| 7,872,959 B2 | 1/2011 | Kimura et al. |
| 2001/0046276 A1 | 11/2001 | Schneider et al. |
| 2004/0032585 A1 | 2/2004 | Johansen et al. |
| 2004/0175174 A1 | 9/2004 | Suhami |
| 2007/0109924 A1 | 5/2007 | Takahashi et al. |
| 2007/0164842 A1 | 7/2007 | Koenig |
| 2007/0165221 A1 | 7/2007 | Deck et al. |
| 2008/0020480 A1 | 1/2008 | Lin et al. |
| 2008/0094631 A1 | 4/2008 | Jung et al. |
| 2008/0119060 A1 | 5/2008 | Goodwin |
| 2009/0161520 A1 | 6/2009 | Hendriks |

OTHER PUBLICATIONS

Y.H. Fan et al., "Switchable Fresnel Lens Using Polymer-stabilized Liquid Crystal", Optics Express 11, 3080-3086 (2003).

M. Honma and T. Nose, "Liquid-Crystal Fresnel Zone Plate Fabricated by Microrubbing", Japanese Journal of Applied Physics, Part I—Regular Paper, Short Papers and Review Papers 44, 287-290 (2005).

T.H. Lin et al., "Polarization Controllable Fresnel lens using dye-doped liquid crystals", Optics Express 14, p. 2359-2364 (2006).

Y. Saito et al., "Laser-induced fluorescence imaging of plants using a liquid crystal tunable filter and charge coupled device imaging camera", Review of Scientific Instruments, 76, 106103 (2005).

J.Y. Hardeberg, et al., "Multispectral color image capture using a liquid crystal tunable filter", Optical Engineering 41, 2532-2548 (2002).

Y. Park et al., "Miniaturization of a fresnel spectrometer", Pure Appl. Opt. 10 (2008) 095301.

P.C. Montgomery, et al., "The metrology of a miniature FT spectrometer MOEMS device using white light scanning interference microscopy", Pure Appl. Opt. 10 (2008) 095301.

* cited by examiner

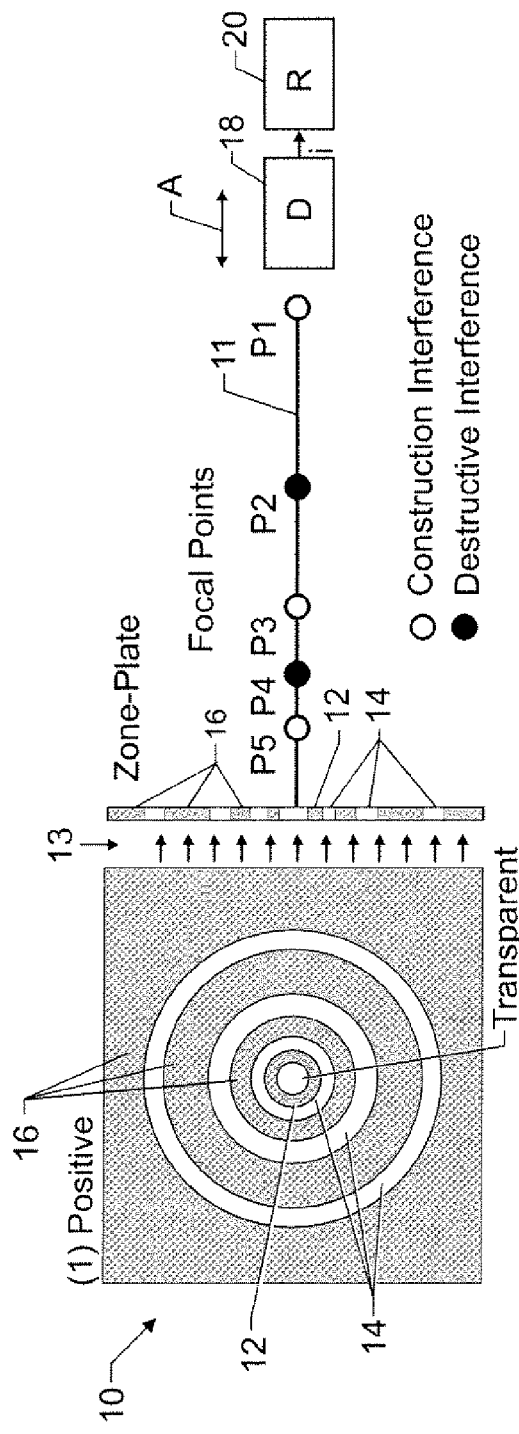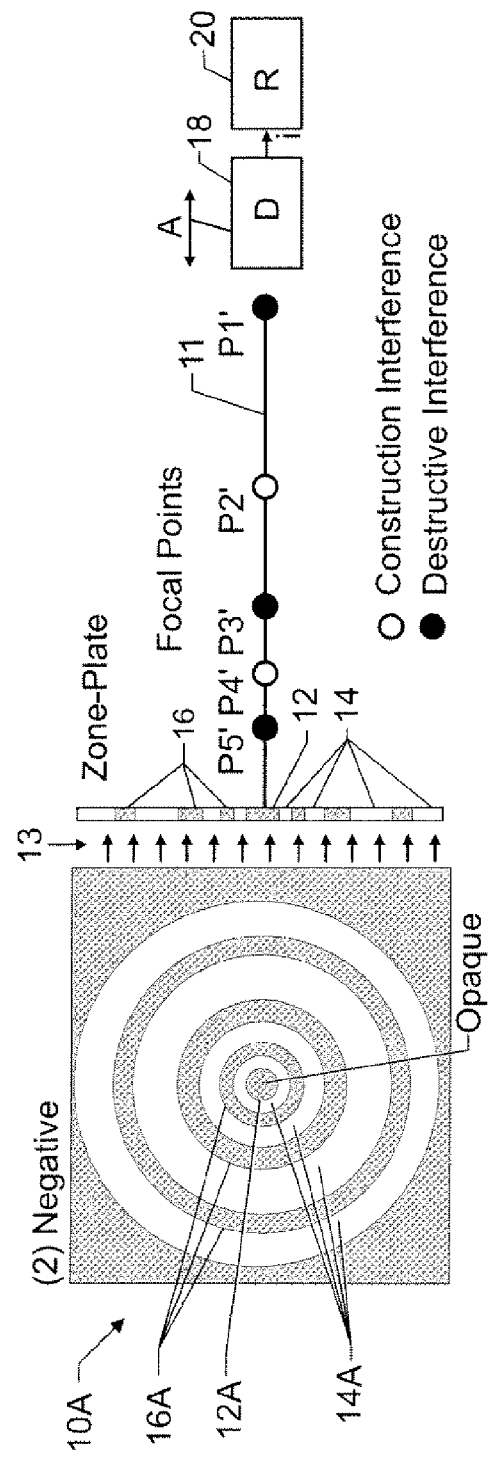

(2)
Micro Zone Plates as
Focused Ring-Grating Array (4)
Photon Detector Array
(p-i-n diodes)

US 8,174,695 B2

ARRAYED MICRO-RING SPECTROMETER SYSTEM AND METHOD OF USE

CROSS-REFERENCE TO RELATED APPLICATIONS

This application claims priority to and the benefit of U.S. Provisional Application 61/089,226 filed on Aug. 15, 2008, which is hereby incorporated by reference in its entirety.

ORIGIN OF TITLE INVENTION

The invention described herein was made by employees of the United States Government and may be manufactured and used by or for the Government for governmental purposes without payment of any royalties thereon or therefor.

TECHNICAL FIELD

The present invention relates generally to spectrometers, and in particular to spectrometers having an array of thin-film micro-zone plates (MZP) suitable for acquiring photons of a specific wavelength from one or more point light sources.

BACKGROUND OF THE INVENTION

Spectroscopic analysis or spectroscopy pertains to the study of the dispersion of light into its component wavelengths. By analyzing the absorption and dispersion of incident light and other radiation by matter, scientists are able to study various properties of the matter such as temperature, mass, luminosity, composition, etc. Optical instruments known as spectrometers are used to measure and study such light dispersion. Spectrometers therefore play an essential role in the study and design of various scientific monitoring devices, for example multi-spectral imaging (MSI) systems, hyper-spectral imaging (HSI) systems, and the like.

In a conventional spectrometer, incident light passes through a first linear opening or slit in a mirror or an optical lens. A beam of incident light passing through the first slit illuminates a prism or a linear grating device. The grating device may have a series of vertically-aligned gratings which diffract the incident light into its component colors, with each color corresponding to a particular band of wavelengths of the electromagnetic spectrum.

Spectrometers may include multiple aperture slits, with the first slit positioned in front of the linear grating device to initially select light in a relatively narrow band of wavelengths. The linear grating device spreads this portion of the light beam at different wavelength-dependent angles. A second slit in another mirror or optical lens may be positioned to allow selective passage of a narrower band of the light beam from the linear grating device. The second slit may be used to direct selected wavelengths to a measurement device to determine a desired spectral characteristic. In this manner, a specific wavelength or set of wavelengths may be selected for detailed spectral analysis.

Conventional spectrometers as described above are often used to acquire and analyze light from a single point source, but may require additional lenses or mirrors to capture a point light source. Because a single spectrometer cannot make a two-dimensional (2D) image without scanning, the total speed of acquiring 2D spectral data is also relatively slow. For example, if it takes approximately 10 seconds to resolve a first spot, 1024×768 images will require 7,864,320 seconds or 91 days to complete. A multi-channel position-sensitive device or Charged Coupled Detector (CCD) array may eliminate the need for a linear aperture slit, but nevertheless may require the additional dimension in order to function properly. A red-green-blue (RGB) CCD array may be used to capture 2D images. However, the color filters of such CCD arrays may have less than optimal spectral resolution.

SUMMARY OF THE INVENTION

Accordingly, a miniature arrayed spectrometer system is provided herein that can be used to rapidly build a high-resolution two-dimensional (2D) image of desired spectral information or data while potentially providing significant size advantages relative to the designs of the prior art. Within the scope of the present invention, the spectrometer system uses an array of photon detectors in conjunction with an array of thin-film micro-ring gratings in the form of micro-zone plates (MZP). The MZP may be configured with an electro-optic layer that can be energized to optimize data acquisition times. The arrayed spectrometer system does not require the use of a focusing lens for micro-objects due to its multiple built-in optical focal points.

In particular, the arrayed spectrometer system includes a plurality of MZP, hereinafter referred to as an MZP array, with each MZP in the MZP array having a plurality of coaxially-aligned annular or ring-shaped gratings. Each MZP diffracts a selected wavelength of incident light from sample matter onto a target focal point, e.g., incident light from a micro/nano object. The spectrometer system also includes a sample layer configured for supporting and illuminating the sample via passage of light through a plurality of apertures, and an array of photon detectors for measuring a desired spectral characteristic of the selected wavelength, e.g., light intensity.

According to one embodiment, each MZP in the MZP array is configured as one of a positive MZP or a negative MZP as those terms are described herein. That is, each MZP in the MZP array is identically configured. An electro-optic layer may be energized to select a wavelength. A beam separator may be positioned adjacent to the MZP array to separate unwanted wavelengths of light from the desired or selected wavelengths.

The sample layer may be configured to emit an exponentially-decaying electrical field or an evanescent wave in response to the incident light, with the evanescent wave exciting molecules of the sample to thereby cause an emission of secondary photons from the sample. These photons are detectable using the array of photon detectors or detector array. A data recorder or other suitable recording device may be placed in communication with the detector array and used to record the intensity of the selected wavelengths or another desired spectral characteristic.

A method of detecting the intensity of selected wavelengths of incident light includes directing the incident light onto an MZP array, with each MZP having a plurality of coaxially-aligned annular or ring-shaped gratings. The gratings are configured for diffracting a predetermined wavelength of light from a sample onto a target focal point. The method includes directing source light onto one side of a sample plate and through a plurality of apertures defined thereby in order to illuminate a sample on the other side of the sample plate. Illumination of the sample generates the incident light, which passes to the MZP array. The MZP array diffracts the selected wavelength(s) onto the target focal point. The method includes detecting the intensity of the selected wavelength(s) using an array of photon detectors.

The above features and advantages and other features and advantages of the present invention are readily apparent from the following detailed description of the best modes for carrying out the invention when taken in connection with the accompanying drawings.

BRIEF DESCRIPTION OF THE DRAWINGS

FIG. 1A is a schematic illustration of a positive micro-zone plate (MZP) usable within an arrayed spectrometer system in accordance with the present invention;

FIG. 1B is a schematic illustration of an alternate negative MZP;

DESCRIPTION OF THE PREFERRED EMBODIMENTS

Figure 5:
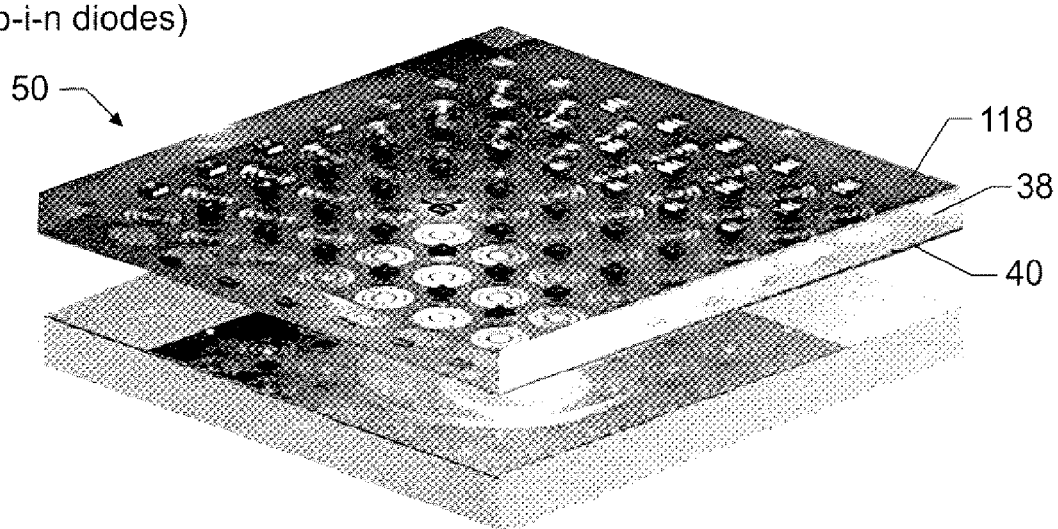
FIG. 5 is a schematic perspective view illustration of a micro-ring thin-film spectrometer system in accordance with the present invention.

Referring to the drawings wherein like reference numbers represent like components throughout the several figures, and beginning with FIG. 1A, a positive electro-optic micro-zone plate (MZP) 10 is provided that can be arrayed with a plurality of similar MZP 10 within the arrayed spectrometer system 50 of the present invention, as shown in FIG. 5 and discussed in further detail hereinbelow. Within the scope of the present invention, the term "MZP" refers to alternating transparent and opaque concentric zones of a predetermined or calibrated width. The MZP 10 may be constructed on a thin film or layer of suitable material, as understood in the art. The MZP 10 can acquire photons of a particular wavelength from multiple point light sources or micro/nano objects, as will described below, and can thereafter build a two-dimensional (2D) image of the detected spectral data.

The positive MAP 10 includes a transparent center disk 12 that is circumscribed by a series of progressively larger transparent rings 14. The transparent rings 14 are separated by an interposed series of progressively larger opaque rings 16, with the center disk 12 and each of the rings being coaxially-aligned and centered on a common optical axis 11. For simplicity, the number of rings is kept at a minimum in FIGS. 1A and 1B, with the actual number of rings depending on the particular design and intended use of the MZP 10.

The transparent center disk 12 and the various rings 14, 16 may be configured as optical gratings on thin film. As will be understood by those of ordinary skill in the art, the term "optical gratings" refers to an optical element configured for diffracting incident light and directing it to a predetermined optical focal point. Gratings have a regular pattern which split and diffract incident light into several beams travelling in directions that depend on the spacing between gratings and the wavelength of the incident light.

Source light (arrows 13) is directed toward the MZP 10 from a source, e.g., a micro/nano object, organism, matter, or other substance serving as the subject of the spectral analysis at hand. The source light is then diffracted by the various rings 14, 16 of the MZP 10 into different wavelengths, with each wavelength directed toward a particular focal point P1, P2, P3, P4, or P5. That is, the particular focal point corresponds to particular wavelengths or frequencies of the source light (arrows 13). The transparent center disk 12 allows a constructive interference point at the farthest focal point, i.e., focal point P1. Additional constructive interference points are provided at focal points P3 and P5.

As is well understood in the art, the transmission of light in the form of waves gives rise to the principals of constructive and destructive wave interference. During any wave interference the shape of the medium is determined by the sum of the separate amplitudes of each wave. The waves interfere when one wave passes through another. When the crest of one wave is superpositioned upon the crest of another, the waves constructively interfere. Constructive interference also occurs when the trough of one wave is superpositioned upon the trough of another. Conversely, destructive interference occurs when the crest of one wave is superpositioned upon the trough of another. During destructive interference, the positive amplitudes from one crest are added to the negative amplitudes from the other trough, with the result being a reduced amplitude or destructive wave interference. Such principles give rise to the different constructive/destructive focal points discussed above.

Referring to FIG. 1B, another type of MZP is the negative MZP 10A, which has at its optical center an opaque center disk 12A that is circumscribed by progressively larger opaque rings 16A. The rings 16A are separated by a corresponding series of progressively larger transparent rings 14A, with the center disk 12A and each of the rings being coaxially-aligned and centered on axis 11. The MZP 10A allows a constructive interference point at P1' but the focused photons at P1' have 180 degree out of phase relation with respect to the focused photons at P1. The source light (arrows 13) is diffracted by the MZP 10A and directed toward a focal point P1', P2', P3', P4', and P5', with the particular focal point corresponding to a band of wavelengths or frequencies of the source Light (arrows 13). The opaque center disk 12A allows a constructive interference point at the farthest focal point, i.e., focal point P1' with photons of 180 degree out of phase. Additional constructive interference points are provided at focal points P3' and P5'.

The MZP 10, 10A may be used as micro-ring gratings that focus parallel photons of source light (arrows 13) into the different radial points according to their wavelengths. A photon detector (D) 18 may be placed at any of the focal points P1-P5, and may relay or transmit detected information (arrow i) to a data recorder (R) 20 to provide a historical record for facilitation of spectral analysis. $0^{th}$ order direct photons from the source light (arrows 13) through the transparent center disk 12 of FIG. 1A may cause bright irregular background noise at the center of circular aperture at a focal point. It takes an infinite number of micro-ring gratings to completely compensate $0^{th}$ order constant photons through the transparent center disk 12 of the positive MZP 10 of FIG. 1A.

This result is similar to the Fourier transform in which y=c (a constant) is approximated by the sum of infinite sine and cosine waves. However, a negative MAP such as the MAP 10A of FIG. 1B does not have a direct line-of-sight between the focal point and the light source, and therefore all converging light is from higher order photons without a $0^{th}$ order photon. Therefore, the MZP 10A of FIG. 1B may be particularly well suited for use as a micro-ring grating due to the opacity of its center disk 12A.

Figure 2:
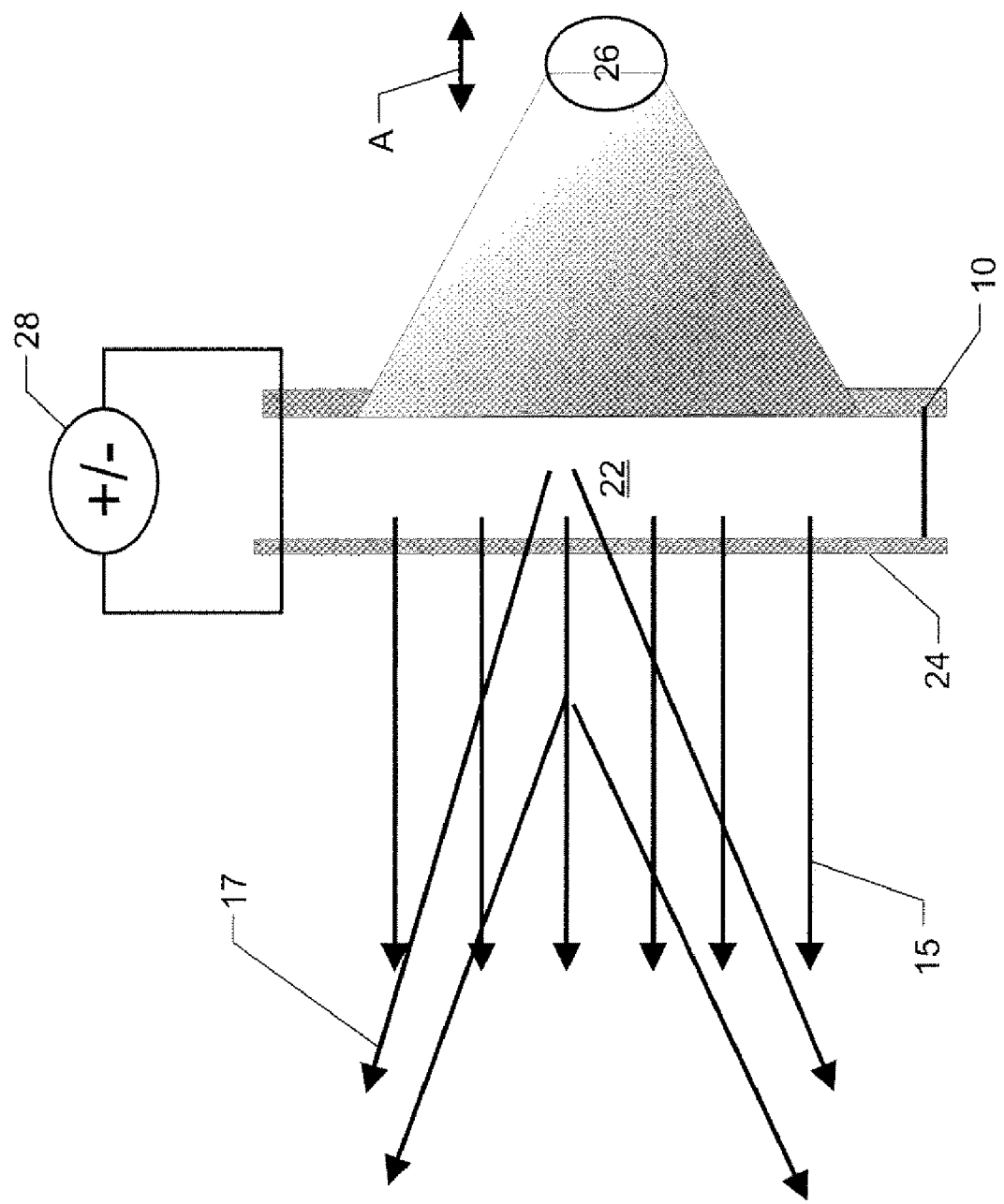
FIG. 2 is schematic illustration of a micro-ring spectrometer usable within the arrayed spectrometer system of the present invention.

Referring to FIG. 2, the MZP 10 of FIG. 1A is used hereinafter to illustrate the core concepts behind the construction of the arrayed spectrometer system 50 of FIG. 5, however the MZP 10A of FIG. 1B may also be used without departing from the intended scope of the invention. In some embodiments, the MZP 10 may be placed adjacent to an electro-optic or E/O layer 22, which in turn may be placed adjacent to a transparent electrode 26. The E/O layer 22 may be constructed of a material have a variable refractive index in response to an applied electric field, e.g., liquid crystal, non-linear crystal, an electro-optic polymer, etc. The electrode 26 in turn provides a bias voltage for the E/O layer 22, and may be constructed of Indium Tin Oxide (ITO) or other suitable materials. The MZP 10 may be fixed, and the designated wavelength (arrows 15) selected by moving a sample 26, e.g. a point light source or micro/nano object, around a focal point as indicated by double-sided arrow A. Non-selected wavelengths (arrows 17) are directed away from the photon detector 18.

For a positive MZP 10 (see FIG. 1A), a good dispersion point is near focal point P1 shown in that Figure. As an MZP already has a built-in focal point, it does not require an additional converging lenses or mirrors of the type used with linear grating systems of the prior art. The MZP 10 may also be included within a programmable spectrometer. In such a configuration, the designated wavelength (arrows 15) may be selected by applying a voltage from a power supply 28 to the E/O layer 22. The sample 26 remains fixed at the focal point in this particular configuration.

Figure 3A:
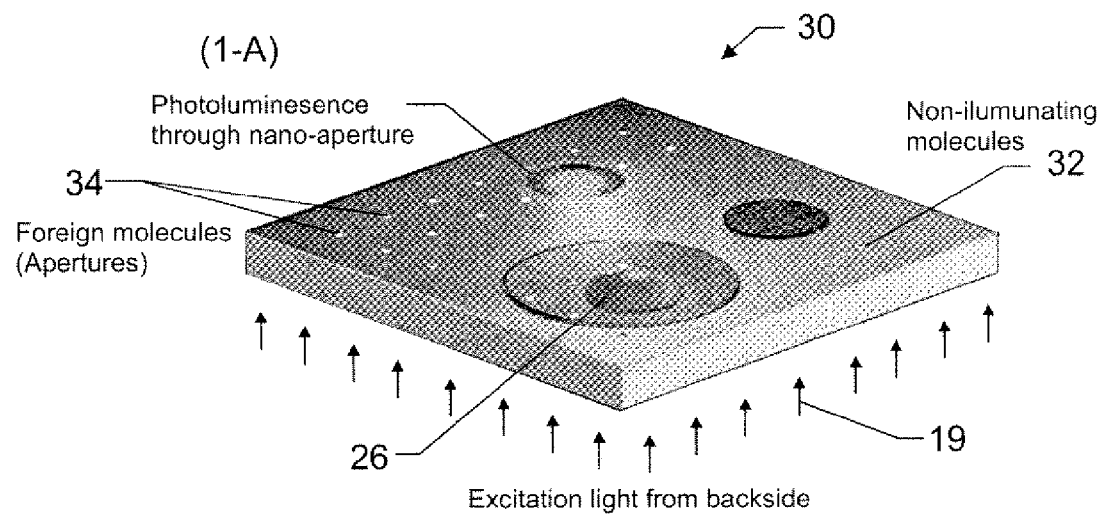
FIG. 3A is a schematic perspective view illustration of a sample layer of the arrayed spectrometer system.

Referring to FIG. 3A, based on the above principles a sample plate 30 may be illuminated using backside light (arrows 19). The sample plate 30 may be constructed as an opaque plate or disk sufficient for supporting the sample 26 on a surface 32. The sample plate 30 defines or includes a series of apertures 34, which in one embodiment are equally-spaced. The apertures 34 may have a diameter of a few nanometers according to one embodiment, and admit some of the backside light (arrows 19) to help define a pixel in the 2D image.

Figure 3B:
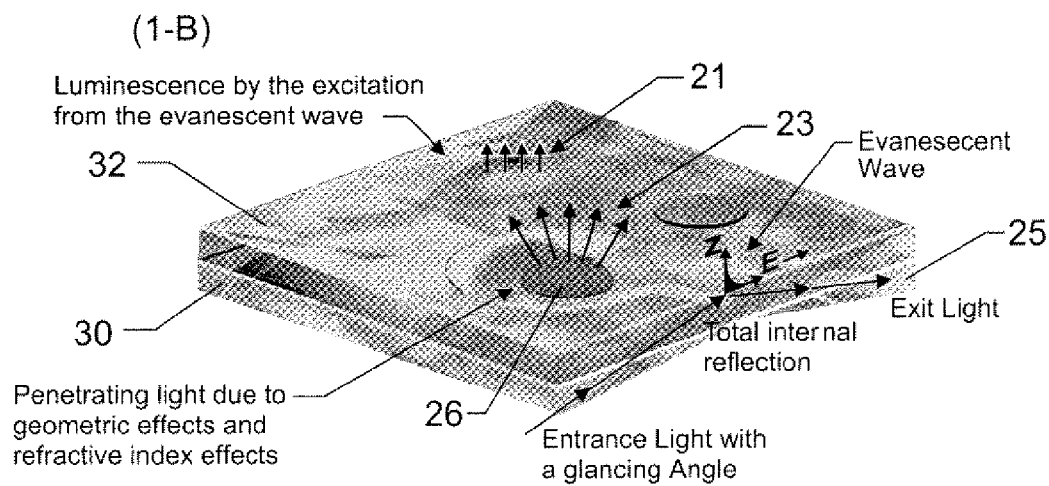
FIG. 3B is another schematic perspective view illustration of the sample layer of FIG. 3A.

Referring to FIG. 3B, the illuminated sample 26 can emit secondary photons (arrows 21) with different wavelengths by a photoluminescence process. Also, different materials and geometric topographies may change the intensity of the penetrating photons (arrows 23) through the apertures 34. The secondary photons (arrows 21) and the penetrating photons (arrows 23) may be detected and measured for spectral analysis of the sample 26.

When backside light (arrow 19) is incident on the sample plate 30 at a glancing angle, total internal reflection occurs so that no photon is able to travel above surface 32. Exit light (arrow 25) is reflected away from the sample plate 30. However, the tangential component of the electric field ($\vec{E}$) is still continuous above the surface 32, and this tangential component decays exponentially with time (t) above the surface 32 as shown in the superimposed graph 36 plotting Z vs. $\vec{E}_\perp$.

This vertically-decaying time-varying electric field is known as the evanescent wave. Because the evanescent wave is decaying quickly along the Z-axis, it cannot reach the photon detector 18 (see FIGS. 1A and 1B) if the detector is positioned at a distance of greater than a few microns from the sample plate 30. However, the evanescent wave can excite the molecules of the sample 26 on the surface 32 to emit the secondary photons (arrows 21), which can travel over a considerable distance. Also, if there are geometric variations due to the sample 26, some of the light, i.e., the penetrating photons of arrows 21, can penetrate and travel above the surface 32 absent total-internal-reflection.

Figure 4:
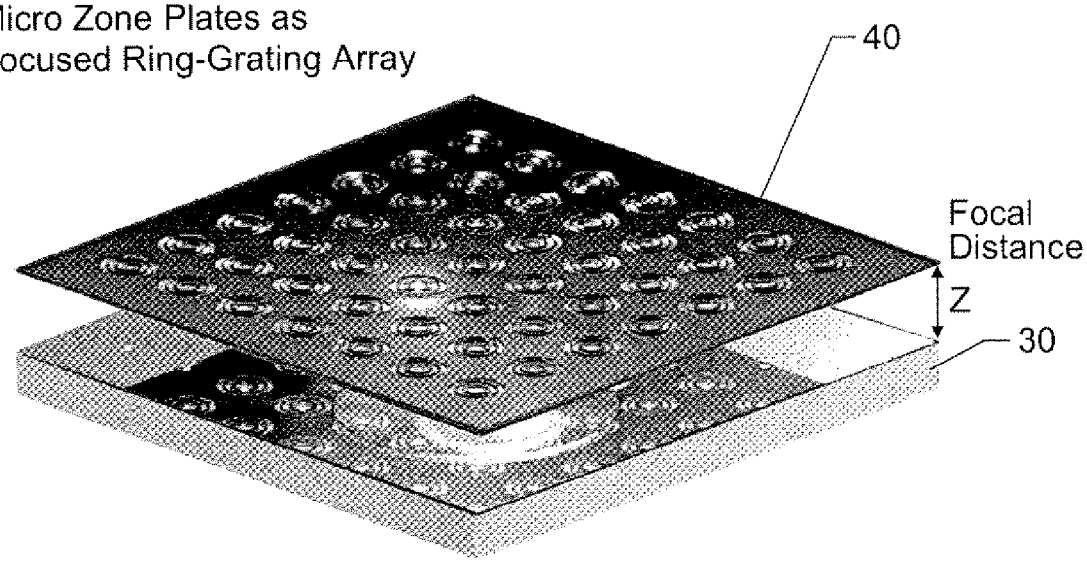
FIG. 4 is a schematic perspective view illustration of an array of MZP and the sample layer of FIG. 3.

Referring to FIG. 4, in order to construct the arrayed spectrometer system 50 of FIG. 5, an MZP array 40 is first positioned above the sample plane 30. The MZP array 40 includes a plurality of individual MZP, whether a positive MZP as shown in FIG. 1A or a negative MZP as shown in FIG. 1B. The MZP array 40 is placed at a focal distance Z above the sample plate 30 supporting the sample 26 that is being spectrally analyzed.

Referring to FIG. 5, the arrayed spectrometer system 50 of the present invention includes a beam separator 38 that is placed adjacent to the MZP array 40 to separate unwanted wavelengths of light. A photon detector array 118 constructed of a plurality of photon detectors 18 (see FIGS. 1A, 1B, and 2) is positioned adjacent the beam separator 38 and opposite the MZP array 40, i.e., the beam separator is sandwiched between the detector array 122 and the MAP array 40. The detector array 122 may be an array of PiN diodes, i.e., diodes having a lightly doped near intrinsic semiconductor region between a p-type and an n-type semiconductor region. Alternately, the array 122 may include M-MOS or P-MOS logic devices, i.e., respective M-type or P-type field effect transistors, a charged-coupled device (CCD) or analog shift register, as those terms are understood in the art. However, other photon detecting devices may also be used without departing from the intended scope of the invention.

The detector array 122 receives light of a specific wavelength from each MZP 10 in the MZP array 40. For a fixed-ring grating MZP, the distance or focal length Z between the plane of the sample plate 30 and the MZP array 40 may be changed to select a different wavelength of light for spectral analysis. As shown in FIG. 2, for an electro-optical ring grating MAP a voltage may be applied to the E/O layer 22 to bring a specific wavelength light to each photon detector 18 in the detector array 118.

While acquisition of point-source light is noted above, those of ordinary skill in the art will readily appreciate that the arrayed spectrometer system 50 can also acquire light from greater distances. That is, each aperture 34 can confine parallel light transmitted over a distance and effectively convert the light to an equivalent point-source. In this manner the system 50 can be used to capture 2D spectral data from far objects, thus enabling a host of potential applications including but not limited to multi-spectral imaging (MSI), hyper-spectral imaging (HSI), and other remote sensing and/or spectral analysis applications.

While the best modes for carrying out the invention have been described in detail, those familiar with the art to which this invention relates will recognize various alternative designs and embodiments for practicing the invention within the scope of the appended claims.

The invention claimed is:

1. An arrayed spectrometer system comprising:
    an array of microzone plates (MZP) each having a plurality of coaxially-aligned ring gratings configured for diffracting a predetermined wavelength of incident light from a sample onto a target focal point;
    an electro-optic layer positioned adjacently to the array of MZP;
    a sample plate configured for supporting the sample, and for passing a portion of source light to the sample to generate the incident light; and
    an array of photon detectors, wherein each photon detector in the array of photon detectors is operable for detecting a spectral characteristic of the predetermined wavelength.

2. The arrayed spectrometer system of claim 1, wherein the predetermined wavelength is selected by applying a voltage to the electro-optic layer.

3. The arrayed spectrometer system of claim 1, further comprising a beam separator positioned adjacently to the array of MZP.

4. The arrayed spectrometer system of claim 1, wherein the sample plate is configured to emit an evanescent wave in response to the source light, wherein the evanescent wave excites molecules of the sample to thereby cause an emission of secondary photons as at least a portion of the incident light.

5. An arrayed spectrometer system comprising:
- an array of micro-zone plates (MZP) each having a plurality of coaxially-aligned ring gratings configured for diffracting a predetermined wavelength of incident light from a sample onto a target focal point;
- a sample plate configured for supporting and illuminating the sample, wherein the sample plate defines a plurality of apertures adapted for passing a portion of source light to the sample as the incident light; and
- an array of photon detectors each operable for measuring an intensity of the predetermined wavelength.

6. The arrayed spectrometer system of claim 5, wherein the plurality of apertures are equally-spaced.

7. The arrayed spectrometer system of claim 5, wherein the array of photon detectors includes at least one of: a PiN diode, a charged-coupled device (CCD), an N-MOS device, and a P-MOS device.

8. The arrayed spectrometer system of claim 5, wherein every one of the MZP in the array of MZP is identically configured as one of a positive MZP and a negative MZP.

9. The arrayed spectrometer system of claim 5, wherein the sample plate is configured to emit an evanescent wave in response to the source light, and wherein the evanescent wave excites molecules of the sample to thereby cause an emission of secondary photons as at least a portion of the incident light.

10. A method of detecting the intensity of a selected wavelength of incident light, the method comprising:
- directing source light onto one side of a sample plate and through a plurality of apertures defined thereby to illuminate a sample positioned on the other side of the sample plate, wherein illumination of the sample generates the incident light;
- directing the incident light onto an array of micro-zone plates (MZP), wherein each MZP in the array of MZP has a plurality of coaxially-aligned ring gratings configured for diffracting the selected wavelength of the incident light onto a target focal point;
- diffracting the selected wavelength onto the target focal point using the array of MZP; and
- detecting the intensity of the selected wavelength using an array of photon detectors.

11. The method of claim 10, further comprising: using a data recorder to record the detected intensity.

12. The method of claim 10, wherein diffracting the selected wavelength includes applying a voltage to an electro-optic layer positioned adjacently to the array of MZP.

13. The method of claim 10, wherein directing the incident light onto an array of MZP includes stimulating an emission of an evanescent wave between the sample plate and the array of MZP.

14. The method of claim 10, wherein detecting the intensity of the selected wavelength using an array of photon detectors includes detecting the intensity using an array of PiN diodes.

* * * * *